US010660960B2

United States Patent
Shih et al.

(10) Patent No.: US 10,660,960 B2
(45) Date of Patent: May 26, 2020

(54) OPHTHALMIC DRUG DELIVERY SYSTEM CONTAINING PHOSPHOLIPID AND CHOLESTEROL

(71) Applicants: TAIWAN LIPOSOME CO. LTD., Taipei (TW); TLC BIOPHARMACEUTICALS, INC., South San Francisco, CA (US)

(72) Inventors: Sheue-Fang Shih, Taipei (TW); Po-Chun Chang, Taipei (TW); Yun-Long Tseng, Taipei (TW); Luke S. S. Guo, South San Francisco, CA (US); Keelung Hong, South San Francisco, CA (US)

(73) Assignees: TAIWAN LIPOSOME CO., LTD., Taipei (TW); TLC BIOPHARMACEUTICALS, INC., South San Francisco, CA (US)

( * ) Notice: Subject to any disclaimer, the term of this patent is extended or adjusted under 35 U.S.C. 154(b) by 102 days.

(21) Appl. No.: 15/888,776

(22) Filed: Feb. 5, 2018

(65) Prior Publication Data
US 2018/0169248 A1    Jun. 21, 2018

Related U.S. Application Data

(63) Continuation of application No. 14/572,062, filed on Dec. 16, 2014, now Pat. No. 9,987,360, which is a continuation of application No. 12/538,435, filed on Aug. 10, 2009, now Pat. No. 8,956,600.

(51) Int. Cl.
| | | |
|---|---|---|
| A61K 39/395 | (2006.01) | |
| A61K 47/28 | (2006.01) | |
| A61K 9/00 | (2006.01) | |
| A61K 31/58 | (2006.01) | |
| A61K 31/7088 | (2006.01) | |
| A61K 31/573 | (2006.01) | |
| A61K 31/198 | (2006.01) | |
| A61K 31/405 | (2006.01) | |
| A61K 38/08 | (2019.01) | |
| A61K 38/16 | (2006.01) | |
| A61K 38/38 | (2006.01) | |
| A61K 47/24 | (2006.01) | |
| C07K 16/22 | (2006.01) | |
| A61K 9/10 | (2006.01) | |
| A61K 9/127 | (2006.01) | |
| A61K 9/19 | (2006.01) | |
| A61K 38/00 | (2006.01) | |
| A61K 39/00 | (2006.01) | |

(52) U.S. Cl.
CPC ............ *A61K 47/28* (2013.01); *A61K 9/0019* (2013.01); *A61K 9/0048* (2013.01); *A61K 9/0051* (2013.01); *A61K 31/198* (2013.01); *A61K 31/405* (2013.01); *A61K 31/573* (2013.01); *A61K 31/58* (2013.01); *A61K 31/7088* (2013.01); *A61K 38/08* (2013.01); *A61K 38/16* (2013.01); *A61K 38/385* (2013.01); *A61K 47/24* (2013.01); *C07K 16/22* (2013.01); *A61K 9/10* (2013.01); *A61K 9/1271* (2013.01); *A61K 9/19* (2013.01); *A61K 38/00* (2013.01); *A61K 2039/505* (2013.01); *C07K 2317/24* (2013.01)

(58) Field of Classification Search
None
See application file for complete search history.

(56) References Cited

U.S. PATENT DOCUMENTS

| | | | | |
|---|---|---|---|---|
| 4,804,539 A | * | 2/1989 | Guo ....................... | A61K 9/127 264/4.3 |
| 2007/0072933 A1 | * | 3/2007 | Peyman ............... | A61K 9/0048 514/414 |
| 2007/0293432 A1 | * | 12/2007 | Furfine ............... | A61K 9/0048 514/8.1 |

FOREIGN PATENT DOCUMENTS

| | | | | |
|---|---|---|---|---|
| TW | 200924794 | | 6/2009 | |
| WO | WO-2008039989 A2 | * | 4/2008 | ............. A61K 9/127 |

* cited by examiner

*Primary Examiner* — Yunsoo Kim
(74) *Attorney, Agent, or Firm* — Leason Ellis LLP

(57) ABSTRACT

An ophthalmic drug delivery system that contains phospholipid and cholesterol for prolonging drug lifetime in the eyes.

19 Claims, 3 Drawing Sheets

Specification includes a Sequence Listing.

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: synthetic peptide

<400> SEQUENCE: 1

His Phe Arg Arg His Leu Cys
1               5

<210> SEQ ID NO 2
<211> LENGTH: 7
<212> TYPE: PRT
<213> ORGANISM: Artificial Sequence
<220> FEATURE:
<223> OTHER INFORMATION: synthetic peptide

<400> SEQUENCE: 2

His Trp Arg Gly Trp Val Cys
1               5
```

OPHTHALMIC DRUG DELIVERY SYSTEM CONTAINING PHOSPHOLIPID AND CHOLESTEROL

BACKGROUND OF THE INVENTION

As the eyes are enclosed organs with slow blood circulation, most therapeutic agents cannot reach them in effective amounts when administered systemically.

To resolve this problem, intravitreal injection has been adopted for ophthalmic delivery of therapeutic agents, particularly to the rear ends of the eyes (e.g., retina and choroid). As a therapeutic agent typically stays in the eyes for a limited period, repetitive intravitreal injections are required to achieve the intended therapeutic effect. However, frequent administration using this invasive approach is highly undesirable.

There is a need for a drug delivery system that prolongs the lifetime of a therapeutic agent in the eyes so as to reduce the times of intravitreal injection required in a treatment.

SUMMARY OF THE INVENTION

The present invention is based on an unexpected discovery that a drug delivery system containing phospholipid and cholesterol significantly prolongs the lifetime of Avastin (an antibody specific to vascular endothelial growth factor) in the eyes.

Accordingly, one aspect of this invention relates to a drug delivery system containing a therapeutic agent (e.g., protein, nucleic acid, or small molecule) and a delivery vehicle that includes phospholipid and cholesterol. The mole percent of cholesterol in the delivery vehicle (e.g., in lyophilized form) can be 5-40% (e.g., 10-33% or 20-25%). The delivery vehicle and the therapeutic agent can be either admixed or separate.

In the drug delivery system of this invention, 50-90% of the therapeutic agent is in non-associated form and the weight ratio of the phospholipid and cholesterol in combination to the therapeutic agent is 5-80 to 1. In one example, the therapeutic agent is an antibody against vascular endothelial growth factor (VEGF) and 60-90% of the antibody is in non-associated form and the weight ratio of the phospholipid and cholesterol in combination to the antibody is 5-40 to 1. In another example, the therapeutic agent is an anti-inflammation molecule (e.g., a corticorsteroid).

The phospholipid in the delivery vehicle described herein can be a mixture of two phospholipids. For example, the phospholipid can be one of 2-dioleoyl-sn-glycero-3-phosphatidylcholine (DOPC), 1-palmitoyl-2-oleoyl-sn-glycero-3-phosphatidylcholine (POPC), soy phosphatidylcholine (SPC), or egg phosphatidylcholine (EPC) mixed with either polyethyleneglycol distearoylphosphatidylethanolamine (PEG-DSPE) or diolelphosphatidylglycerol (DOPG). When the phospholipid is a mixture of DOPC and DOPG, the mole percent of the former can be 29.5-90% (e.g., 50-80%) and the mole percent of the latter can be 3-37.5% (e.g., 3-18.75%) In one example, the delivery vehicle contains DOPC, DOPG, and cholesterol at a mole percent ratio of 56.25-72.5:7.5-18.75:20-25.

Another aspect of this invention relates to a method of delivering a therapeutic agent to an eye of a subject. This method includes (i) providing the drug delivery system described above, which can be in aqueous suspension form, and (ii) administering it to an eye of a subject in need by, e.g., intravitreal injection. The delivery system can be prepared by mixing phospholipid, cholesterol, and one or more therapeutic agent to form a mixture; lyophilizing the mixture; and, before administration, suspending the mixture in an aqueous solution to form the aqueous suspension. Alternatively, it is prepared by mixing phospholipid and cholesterol to form a mixture; lyophilizing the mixture; and, before administration, suspending the mixture together with one or more therapeutic agent in an aqueous solution to form the aqueous suspension.

Also within the scope of this invention is use of the delivery vehicle described above in delivering a therapeutic agent ophthalmically and in manufacturing a medicament for treating an ophthalmic disease.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The drawings are first described.

DETAILED DESCRIPTION OF THE INVENTION

Figure 1:
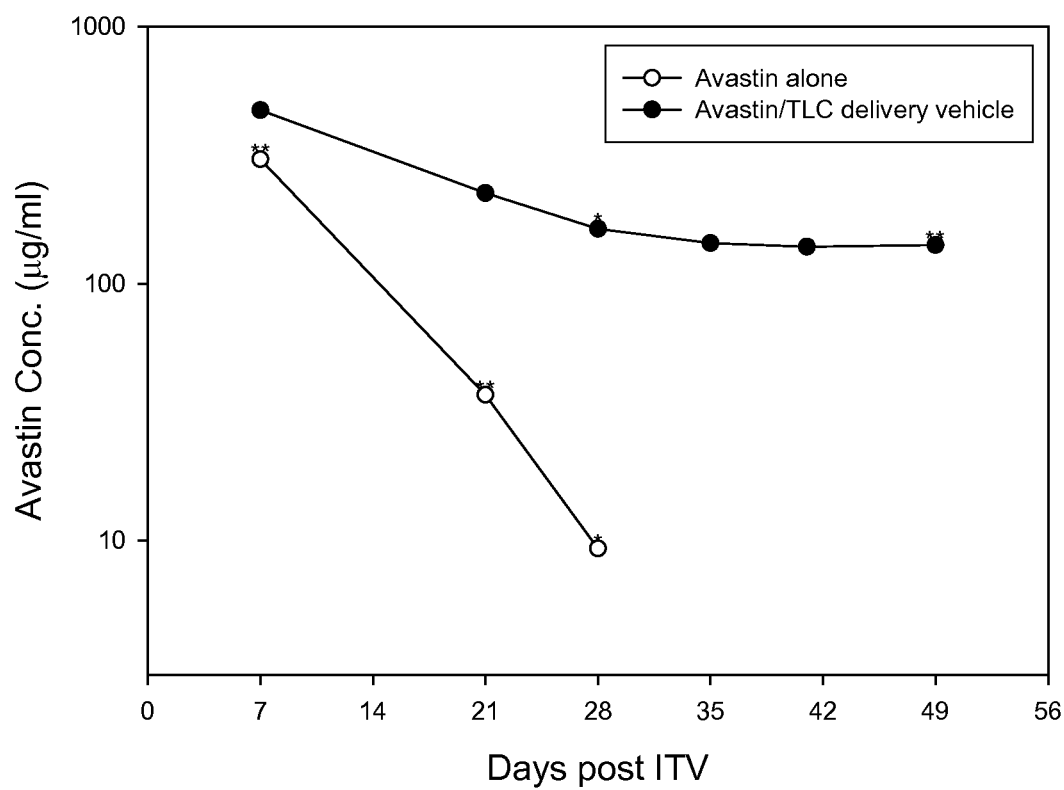
FIG. 1 is a chart showing vitreous Avastin concentrations at days 7, 21, 28, 35, 41, and 49 after intravitreal injection. TLC delivery vehicle refers to a delivery vehicle containing DOPC/Cholesterol/DOPG at a ratio 67.5/25/7.5. "*" and "**" refer to the time points, at which 1 and 2 rabbit eyes were examined, respectively. 4 rabbit eyes were examined at the other time points.

Described herein is an advantageous drug delivery system for ophthalmic administration of at least one therapeutic agent, which upon delivery, exhibits extended lifetime in the eyes, particularly, in vitreous.

Delivery Vehicle

This drug delivery system described herein includes a delivery vehicle containing phospholipid and cholesterol. The phospholipid can be a homologous population of a phospholipid, preferably a neutral phospholipid, or a mixture of different types of phospholipids. Examples of phospholipid for making the delivery vehicle include, but are not limited to, phosphatidylcholine (PC), phosphatidylglycerol (PG), phosphatidylethanolamine (PE), phosphatidylserine (PS), phosphatidic acid (PA), phosphatidylinositol (PI), egg phosphatidylcholine (EPC), egg phosphatidylglycerol (EPG), egg phosphatidylethanolamine (EPE), egg phosphatidylserine (EPS), egg phosphatidic acid (EPA), egg phosphatidylinositol (EPI), soy phosphatidylcholine (SPC), soy phosphatidylglycerol (SPG), soy phosphatidylethanolamine (SPE), soy phosphatidylserine (SPS), soy phosphatidic acid (SPA), soy phosphatidylinositol (SPI), dipalmitoylphosphatidylcholine (DPPC), 1,2-dioleoyl-sn-glycero-3-phosphatidylcholine (DOPC), dimyristoylphosphatidylcholine (DMPC), dipalmitoylphosphatidylglycerol (DPPG), diolelphosphatidylglycerol (DOPG), dimyristoylphosphatidylglycerol (DMPG), hexadecylphosphocholine (HEPC), hydrogenated soy phosphatidylcholine (HSPC), distearoylphosphatidylcholine (DSPC), distearoylphosphatidylglycerol (DSPG), dioleylphosphatidylethanolamine (DOPE), palmitoylstearoylphosphatidylcholine (PSPC), palmitoylstearoylphosphatidylglycerol (PSPG), monooleoylphosphatidylethanolamine (MOPE), 1-palmitoyl-2-oleoyl-sn-glycero-3-phosphatidylcholine (POPC), polyethyleneglycol distearoylphosphatidylethanolamine (PEG-DSPE), dipalmitoylphosphatidylserine (DPPS), 1,2-dioleoyl-sn-glycero-3-phosphatidylserine (DOPS), dimyristoylphosphatidylserine (DMPS), distearoylphosphatidylserine (DSPS), dipalmitoylphosphatidic acid (DPPA), 1,2-dioleoyl-sn-glycero-3-phosphatidic acid (DOPA), dimyristoylphosphatidic acid (DMPA), distearoylphosphatidic acid (DSPA), dipalmitoylphosphatidylinositol (DPPI), 1,2-dioleoyl-sn-glycero-3-phosphatidylinositol (DOPI), dimyristoylphosphatidylinositol (DMPI), distearoylphosphatidylinositol (DSPI), and a mixture thereof.

In one example, the delivery vehicle is free of fatty acid (i.e., carboxylic acid with a long unbranched aliphatic tail), cationic lipid (i.e., lipid carrying a net positive charge at physiological pH); and mucoadhesive polymer (e.g., Carbopol 934 P, polyaxomer, carbomer, and plant lectin).

The delivery vehicle can be prepared by methods known in the pharmaceutical industry. An example follows. Phospholipid, cholesterol, and other components, if any, is suspended in distilled water or an aqueous solution to form a suspension. The suspension is then subjected to homogenization by conventional methods, e.g., sonication, shaking, or extrusion. After being sterilized, the homogenized vehicle suspension can be placed aseptically in a container and then lyophilized to form a powder.

Therapeutic Agent

Any therapeutic agents (e.g., small molecule, protein, peptide, or nucleic acid) for treating ophthalmic disease can be mixed with the delivery vehicle described above and administered to an eye of a subject. In one example, the therapeutic agent is an anti-inflammation drug, such as a corticosteroid compound. The term "corticosteriod compound" refers to naturally occurring steroid hormones (including glucocorticoids) and their derivatives, which preferably are water soluble. Examples of corticosteriod include, but are not limited to, cortisone, hydrocortisone, hydrocortisone acetate, tixocortol pivalate, flucinolone, prednisolone, methylprednisolone, prednisone, triamcinolone acetonide, triamcinolone, mometasone, amcinonide, budesonide, desonide, fluocinonide, fluocinolone acetonide, halcinonide. betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate. In another example, the agent is an antagonist of VEGF, which can be an antibody specific to VEGF, a soluble VEGF receptor, a nucleic acid binding to VEGF, or a small molecule that interferes with the interaction between VEGF and its cognate receptor and blocks the VEGF signaling pathway. The term "antibody" used herein refers to a naturally-occurring immunoglobulin, a functional fragment thereof, such as Fab, Fab', F(ab)$_2$ or F(ab')$_2$, or a genetically modified immunoglobulin, such as humanized antibody, chimeric antibody, diabody, and single-chain antibody.

Drug Delivery System

The drug delivery system of this invention includes the delivery vehicle described above and one or more of the therapeutic agents also described above. It can contain a vehicle-drug mixture in lyophilized form. In one example, the mixture is prepared by suspending all components of the vehicle in water or an aqueous solution to form a suspension, homogenizing the suspension, mixing the homogenized suspension with one or more therapeutic agents to form a mixture, and finally lyophilizing the mixture. In another example, the mixture is prepared by suspending all components of the vehicle and the one or more therapeutic agents in water or an aqueous solution to form a suspension and then lyophilizing the suspension to form a lyophilized mixture. A cryoprotectant (e.g., mannitol, sucrose, trehalose, and lactose) can be added to the vehicle-drug suspension during lyophilization. When mannitol is used, the preferred concentration range is 0.5-5% (e.g., 0.5-2% or 1%). Before administration, the lyophilized vehicle-drug mixture is re-suspended in an aqueous solution, which can then be delivered to an eye of a subject.

In this drug delivery system, 50-90% of the therapeutic agent is in non-associated form. The term "therapeutic agent in non-associated form" refers to the therapeutic molecules separable via gel filtration from the phospholipid/cholesterol fraction of the delivery system. The percentage of the non-associated therapeutic agent is determined following the method described in Example 7 below.

Optionally, the drug delivery system of this invention can further include a pharmaceutically acceptable carrier, i.e., a carrier compatible with the therapeutic agent in the system, and preferably, capable of stabilizing the therapeutic agent and not deleterious to the subject to be treated.

The above-described drug delivery system can be administered to an eye of a subject via, e.g., intravitreal injection, for treating ophthalmic diseases.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

Example 1: Preparation of Phospholipid-Cholesterol-Containing Compositions for Drug Delivery in Eyes Phospholipids DOPC and DOPG were mixed with cholesterol at various molar ratios (i.e., 67.5:7.5:25, 72:8:20, and 56.25:18.75:25) to form lipid mixtures. The mixtures were suspended in chloroform and dried under vacuum in a rotary evaporator. Each of the dried mixtures was re-suspended in deionized H$_2$O, homogenized by a cup horn sonicator (Misonix Sonicator 3000), and then sterilized using a sterile filter. The sterilized lipid mixtures were filled aseptically into vials, mixed with 1% mannitol, and then lyophilized. The total concentration of the phospholipids in each of the lyophilized mixtures was determined by a phosphorus assay. Before delivery to the eyes, a suitable amount of a lipid mixture mentioned above was mixed with a suitable amount of Avastin and suspended in an aqueous solution to form an aqueous suspension.

Example 2: Use of DOPC/PEG-DSPE/Cholesterol-Containing Delivery Vehicles for Delivering Avastin to Eyes Delivery vehicles containing DOPC, PEG-DSPE, and cholesterol at various molar ratios were prepared following the method described in Example 1 above. Each of these delivery vehicles were mixed with a suitable amount of Avastin to form aqueous suspensions.

The effect of the delivery vehicles mentioned above in prolonging the lifetime of Avastin in eyes was examined following the method described in Bakri et al., Ophthalmology, 2007, 114:5, 855-859. Briefly, New Zealand White rabbits were sedated by intramuscular injection of a mixture containing Zoletil (15 mg/ml) and Rompun (7 mg/ml). Both eyes of each rabbit were injected intravitreally with 50 µl of Avastin (25 mg/ml) or one of the aqueous suspensions mentioned above (at an Avastin dose of 1.25 mg per eye) using a 30-gauge needle. Rabbits were sacrificed at 7 days or 21 days after injection and their eyes were promptly enucleated. The vitreous humor was isolated from each eye together with retina and Avastin concentration was determined by ELISA as follows.

A F96 MaxiSorp™ NUNC-IMMUNO plate was coated with VEGF (10 µg/ml in PBS, pH 7.4; 100 µl/well) at 4° C. overnight. The VEGF-coated plate was washed with PBS and then blocked with a blocking buffer (5% skim milk in PBS) at room temperature for 1 hour. The vitreous humor/retina samples mentioned above were diluted in the same blocking buffer and the resultant diluents were added to the VEGF-coated plate at 100 µl/well. After being incubated at room temperature for 1 hour, the plate was washed with 0.1% Tween-20 and 0.5% skim milk in PBS for 5 times and with PBS for another 5 times. HRP-labeled goat anti-human IgG (Jackson ImmunoResearch Lab. Inc.), diluted in the blocking buffer, was then added to the plate. After being incubated at room temperature for 30 minutes, the plate was washed extensively. A tetramethyl benzidine-containing reagent was then added to the plate for color development. After a sufficient period, the reaction was terminated by addition to each well 50 µl 2 N HCl. The absorbance at 450 nm ($OD_{450}$) of each well was determined by an ELISA reader. Various pre-determined Avastin concentrations (3.125-25 ng/ml) were used to establish a standard Avastin concentration/$OD_{450}$ curve. The Avastin concentration in each sample was determined based on its $OD_{450}$ value in view of the standard curve.

The results obtained from this study are shown in Table 1 below:

TABLE 1

Concentrations of Avastin Delivered by Vehicles Containing DOPC/PEG-DSPE/Cholesterol at Various Molar Ratios Seven Days After Intravitreal Injection

| | Avastin Concentration (µg/ml) |
|---|---|
| Avastin | 247 ± 27 |
| Avastin + DOPC/PEG-DSPE (97/3)* | 234 ± 21 |
| Avastin + DOPC/CHOL/PEG-DSPE (70/25/5)* | 632 ± 75 |
| Avastin + DOPC/CHOL/PEG-DSPE (55/40/5)* | 354 ± 91 |
| Avastin + DOPC/CHOL/PEG-DSPE (74.5/25/0.5)* | 688 ± 16 |

*The numbers in brackets refer to the mole percents of the phospholipids and cholesterol As shown in Table 1 above, Avastin stayed in the eyes for a longer time period when co-delivered with the DOPC/PEG-DSPE/cholesterol-containing vehicles as compared to Avastin delivered alone. The results also indicate that cholesterol is essential to the effect of the delivery vehicle in extending the lifetime of Avastin in the eyes and the molar percent of PEG-DSPE does not affect this effect.

Example 3: Use of Delivery Vehicles Containing Various Phospholipids for Prolonging Lifetime of Avastin in Eyes Delivery vehicles containing various phospholipids and cholesterol at different molar ratios were prepared following the method described in Example 1 above. The vehicles were mixed with Avastin and the resultant mixtures were injected into the eyes of New Zealand rabbits intravitreally. 7 or 21 days after the injection, the Avastin concentrations in the rabbits' eyes were examined following the method described in Example 2 above. Results thus obtained are shown in Tables 2 and 3 below:

TABLE 2

Concentrations of Avastin Delivered by Vehicles Containing Different Phospholipids and Cholesterol Seven Days After Intravitreal Injection

| | Avastin Concentration (µg/ml) |
|---|---|
| Avastin | 247 ± 27 |
| Avastin + DOPC/CHOL/PEG-DSPE (74.5/25/0.5)* | 688 ± 16 |
| Avastin + POPC/CHOL/PEG-DSPE (74.5/25/0.5)* | 572 ± 32 |
| Avastin + SPC/CHOL/PEG-DSPE (74.5/25/0.5)* | 746 |

*The numbers in brackets refer to the mole percents of the phospholipids and cholesterol

TABLE 3

Concentrations of Avastin Delivered by Vehicles Containing Cholesterol and Different Phospholipids Twenty-One Days After Intravitreal Injection

| | Avastin Concentration (µg/ml) |
|---|---|
| Avastin | 37 ± 7 |
| Avastin + DOPC/CHOL/PEG-DSPE (74.5/25/0.5)* | 41 ± 6 |
| Avastin + DOPC/CHOL/PEG-DSPE (55/40/5)* | 48 ± 9 |
| Avastin + EggPC/CHOL/PEG-DSPE (74.5/25/0.5)* | 155 ± 64 |

*The numbers in brackets refer to the mole percents of the phospholipids and cholesterol Example 4: Use of Delivery Vehicles Containing Anionic Phospholipids for Prolonging Lifetime of Avastin in Eyes Delivery vehicles containing DOPG, an anionic phospholipid, PEG-DSPE or DOPC, with or without cholesterol were prepared following the method described in Example 1 above. These vehicles were mixed with Avastin and the resultant mixtures were injected into the eyes of New Zealand rabbits intravitreally. 7 or 21 days after the injection, the Avastin concentrations in the rabbits' eyes were examined following the method described in Example 2 above.

As shown in Table 4 below, the delivery vehicle containing the anionic phospholipid DOPG led to an increased Avastin concentration 7 days after injection as compared to the delivery vehicle that does not contain DOPG.

TABLE 4

Vitreous Concentration of Avastin Delivered by Vehicles
Containing anionic phospholipids Seven Days After Injection

|  | Avastin Concentration (μg/ml) |
|---|---|
| Avastin | 247 ± 27 |
| Avastin + DOPC/PEG-DSPE (97/3)* | 234 ± 21 |
| Avastin + DOPC/DOPG (90/10)* | 371 ± 16 |

*The numbers in brackets refer to the mole percents of the phospholipids

The results obtained from this study also indicate that delivery vehicles containing cholesterol and DOPG dramatically increased the vitreous Avastin concentration 21 days after injection. See Table 5 below.

TABLE 5

Vitreous Concentration of Avastin Delivered by Vehicles Containing
anionic phospholipids and Cholesterol 21 Days After Injection

|  | Avastin Concentration (μg/ml) |
|---|---|
| Avastin | 37 ± 7 |
| Avastin + DOPC/CHOL/PEG-DSPE (74.5/25/0.5) | 41 ± 6 |
| Avastin + DOPC/CHOL/DOPG (67.5/25/7.5) | 225 ± 21 |

*The numbers in the brackets refer to the mole percents of the phospholipids and cholesterol

Example 5: Use of Delivery Vehicles Containing Cholesterol at Various Mole Percents Anionic for Prolonging Lifetime of Avastin in Eyes Delivery vehicles containing cholesterol at various mole percents, DOPC, and DOPG were prepared following the method described in Example 1 above. These vehicles were mixed with Avastin and the resultant mixtures were injected into the eyes of New Zealand rabbits intravitreally. 21 days after the injection, the Avastin concentrations in the rabbits' eyes were examined following the method described in Example 2 above. The results obtained from this study are shown in Table 6 below:

TABLE 6

Vitreous Concentration of Avastin Delivered by Vehicles
Containing Cholesterol 21 Days After Injection

|  | Avastin Concentration (μg/ml) |
|---|---|
| Avastin | 37 ± 7 |
| Avastin + DOPC/CHOL/DOPG (81/10/9)* | 51 ± 53 |
| Avastin + DOPC/CHOL/DOPG (72/20/8)* | 198 ± 131 |
| Avastin + DOPC/CHOL/DOPG (67.5/25/7.5)* | 225 ± 21 |
| Avastin + DOPC/CHOL/DOPG (60/33/7)* | 58 ± 6 |
| Avastin + DOPC/CHOL/DOPG (56.25/25/18.75)* | 185 ± 85 |
| Avastin + DOPC/CHOL/DOPG (37.5/25/37.5)* | 65 ± 39 |
| Avastin + DOPC/CHOL/DOPG (18.75/25/56.25)* | 25 |
| Avastin + DOPC/CHOL/DOPG (7.5/25/67.5)* | 68 ± 22 |
| Avastin + CHOL/DOPG (25/75)* | 130 ± 45 |

*The numbers in the brackets refer to the mole percents of the phospholipids and cholesterol

Example 6: Pharmacokinetic Properties of Avastin Delivered to Vitreous by Vehicles Containing Phospholipid and Cholesterol Rabbits were injected intravitreally with either Avastin alone (control rabbits) or Avastin mixed with a delivery vehicle containing DOPC/Cholesterol/DOPG at a ratio 67.5/25/7.5 (test rabbits). Vitreous Avastin concentrations of the control rabbits were examined by ELISA at days 7, 21, and 28 post injection and those of the test rabbits were examined at days 7, 21, 28, 35, 41, and 49 post injection.

The vitreous concentration of Avastin injected alone decreased much rapidly over time than that of Avastin injected with the delivery vehicle. See FIG. 1. This result demonstrates that the delivery vehicle prolongs the lifetime of Avastin in eyes.

Figure 2:
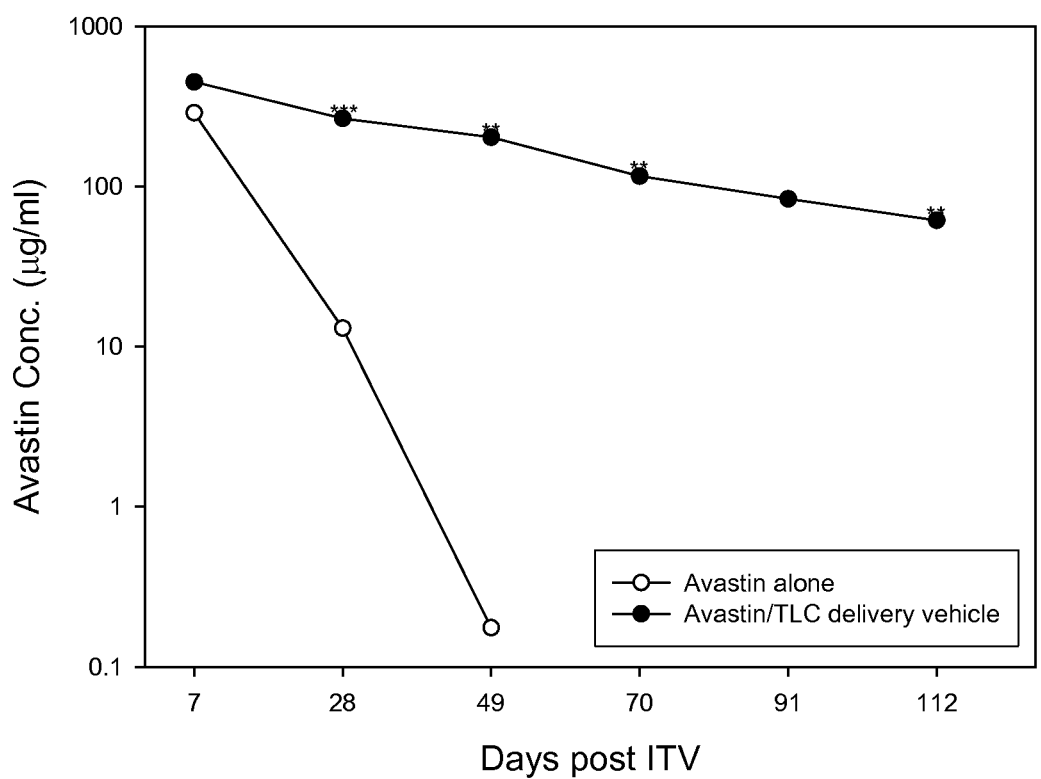
FIG. 2 is a chart showing vitreous Avastin concentrations at days 7, 28, 49, 70, 91 and 112 after intravitreal injection. TLC delivery vehicle refers to a delivery vehicle containing DOPC/Cholesterol/DOPG at a ratio 67.5/25/7.5. "" and "*" refer to the time points, at which 2 and 3 rabbit eyes were examined, respectively. 4 rabbit eyes were examined at the other time points.

In a similar study, the vitreous Avastin concentrations were monitored 7, 28, 49, 70, 91 and 112 days post intravitreal injection. For the control rabbits, the vitreous Avastin concentration was 13 μg/ml 28 days after the injection, while for the test rabbits, the vitreous Avastin concentration at the same time point was 265 μg/ml, 20-times higher than that of the control rabbits. See FIG. 2. The half-life of intravitreal Avastin in the control rabbits is 3.9 days. Differently, the half-life of intravitreal Avastin in the test rabbits exhibits a 2-compartment characteristic with the initial and the terminal half-lives being 5.5 ($t_{1/2\alpha}$) and 40.5 ($t_{1/2\beta}$) days, respectively. The AUC (i.e., area under curve) of Avastin from the $7^{th}$ day to infinity ($AUC_{(7-\infty)}$) in the test rabbits is 6.8-fold higher than that of the control rabbits and the $AUC_{(112-\infty)}$ of Avastin in the test rabbits is 1.1-fold higher than the $AUC_{(7-\infty)}$ of Avastin in the control rabbits. See Table 7 below.

TABLE 10

Pharmacokinetic Properties of Vitreous Avastin

|  | Control Rabbits | Test Rabbits |
|---|---|---|
| $t_{1/2}$ (days)* | 3.9 | 5.5 ($t_{1/2\alpha}$)** |
|  |  | 40.5 ($t_{1/2\beta}$)† |
| $AUC_{(7-112)}$†† (d · μg/ml) | 3294 | 18758 |
| $AUC_{(112-\infty)}$‡ (d · μg/ml) | 0 | 3585 |
| $AUC_{(7-\infty)}$‡‡ (d · μg/ml) | 3294 | 22343 |

*$t_{1/2}$: half-life;
**$t_{1/2\alpha}$: initial half-life;
†$t_{1/2\beta}$: terminal half-life;
††$AUC_{(7-112)}$: area under the curve from the $7^{th}$ day to the $112^{th}$ day;
‡$AUC_{(112-\infty)}$: area under the curve from the $112^{th}$ day to infinity;
‡‡$AUC_{(7-\infty)}$: area under the curve from the $7^{th}$ day to infinity.

In sum, the results discussed above demonstrate that the delivery vehicle significantly prolonged the lifetime of Avastin in eyes.

Example 7: Preparation of Compositions for Delivering Various Therapeutic Agents DOPC, DOPG, and cholesterol at a weight ratio of 8.8/1/1.6 were dissolved in chloroform, which was then evaporated under vacuum using a rotary evaporator. The dried mixture of the phospholipids and cholesterol thus produced was suspended in deionized water to form an aqueous suspension. The suspension is then homogenized via sonication using a cup horn sonicator (Misonix Sonicator 3000), sterilized by filtration, filled aseptically in a vial, and lyophilized to form a phospholipid-cholesterol-containing delivery vehicle. The phospholipid concentration in the vehicle was determined by a conventional phosphorus assay to ensure that the vehicle contained an appropriate total amount of the phospholipids.

The delivery vehicle was then mixed with various therapeutic agents, i.e., tryptophan (10 mg/ml), tyrosine (10.4 mg/ml), HFRRHLC (SEQ ID NO: 1) peptide (10 mg/ml), HWRGWVC (SEQ ID NO: 2) peptide (10 mg/ml), protein W (13 mg/ml), bovine serum albumin (50 mg/ml), Avastin (25 mg/ml) and dexamethasone sodium phosphate (6.7 mg/ml), all dissolved in 50 mM phosphate butter, pH 6.2. The mixtures thus formed were diluted 18-100-fold in the same phosphate buffer and an aliquot of each mixture (50-200 ml) was subjected to gel-filtration to determine the percentage of the therapeutic agent that was in non-associated form. Briefly, an aliquot of a mixture was loaded onto a Sepharose 4B column (diameter: 1.8 mm; length: 315 mm). The components in the mixture were then eluted by 50 mM phosphate buffer (pH 6.2). Fractions containing the therapeutic agent in different form, i.e., non-associated form or associated with the phospholipids, were collected, their absorbance being measured at 215 nm and 254 nm. The amount of the therapeutic agent in each fraction was determined based on the values of $OD_{215}$ and $OD_{254}$. Based on these values, the percentages of the non-associated therapeutic agents and the weight ratios of lipids to drugs were determined and shown in Table 11 below.

TABLE 11

Percentages of Non-Associated Drugs agents and Weight Ratio of Lipids to Drugs

| Drugs | Percentage of Non-Associated Drug (%±S.D.) | Weight Ratio of Phospholipid and Chol to Drugs |
|---|---|---|
| Tryptophan | 86.1 ± 0.8 | 69:1 |
| Tyrosine | 80.3 ± 0.1 | 50:1 |
| HWRGWVC (SEQ ID NO: 2) peptide | 52.4 ± 0.2 | 21:1 |
| HFRRHLC (SEQ ID NO: 1) peptide | 71.9 ± 0.2 | 35:1 |
| Protein W | 81.4 ± 0.2 | 41:1 |
| Bovine Serum albumin | 87.2 ± 0.4 | 15:1 |
| Avastin | 62.1 ± 0.9 | 10:1 |
| Dexamethasone sodium phosphate | 68.5 ± 0.5 | 73:1 |

Example 8: Pharmacokinetic Properties of Dexamethasone Sodium Phosphate Delivered to Vitreous by Vehicles Containing Phospholipid and Cholesterol Rabbits were injected intravitreally with either dexamethasone sodium phosphate (DSP) alone (control rabbits) or DSP mixed with a delivery vehicle containing DOPC/Cholesteroll/DOPG at a ratio 67.5/25/7.5 (test rabbits). Both eyes of each rabbit were injected intravitreally with 50 µl of DSP or the DSP-delivery vehicle mixture at a DSP dose of 0.2 mg. Vitreous DSP concentrations of the control rabbits were examined by ultra-performance liquid chromatography (ACQUITY UPLC™) with a photodiode array (PDA) detector at 2 h, 1 d, 4 d, 8 d, and 15 d after the injection and those of the test rabbits were examined at 2 h, 1 d, 4 d, 8 d, 15 d, and 35 d post injection. Two eyes were examined for each time point.

Figure 3:
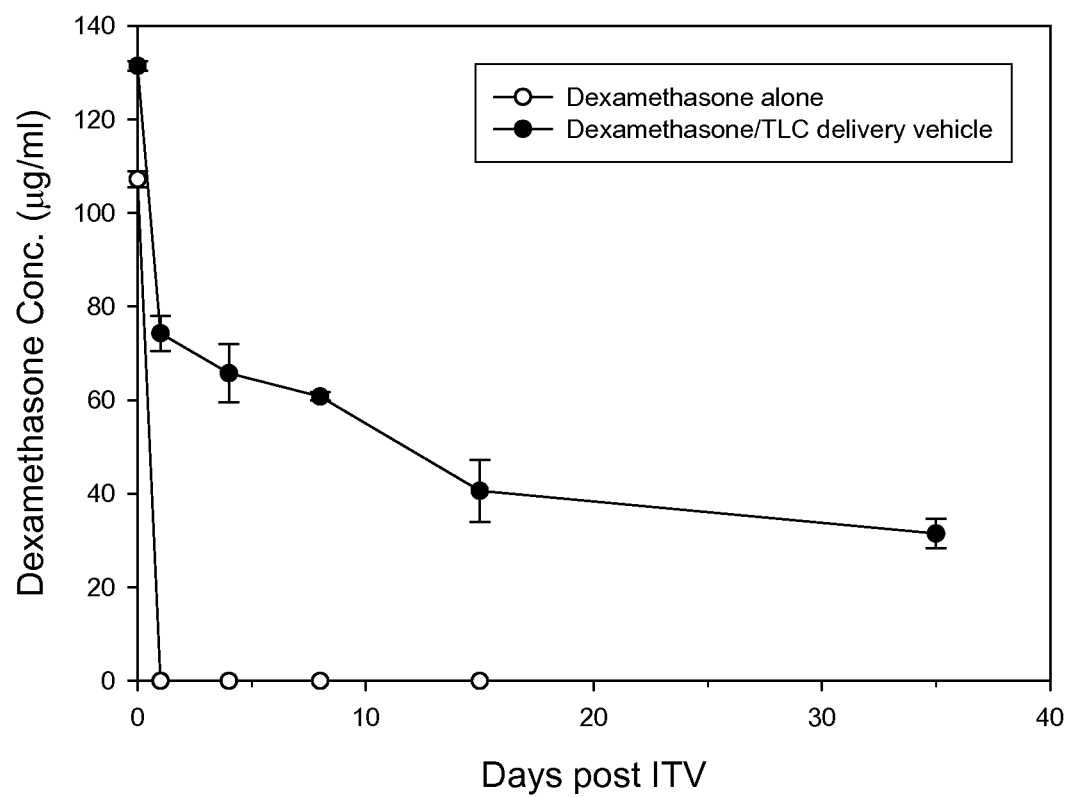
FIG. 3 is a chart showing vitreous dexamethasone sodium phosphate (DSP) concentrations at 2 h, 1 d, 4 d, 8 d, 15 d, and 35 d after intravitreal injection. TLC delivery vehicle refers to a delivery vehicle containing DOPC/Cholesterol/DOPG at a ratio 67.5/25/7.5.

As shown in FIG. 3, the vitreous concentration of DSP injected alone decreased very rapidly after injection; to the contrary, a significant level of DSP injected together with the delivery vehicle was observed even 35 days after injection. This result demonstrates that the delivery vehicle prolongs the lifetime of DSP in eyes.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for delivering a therapeutic agent to an eye of a subject by intravitreal injection, which comprises:
   providing a composition comprising:
   (a) a delivery vehicle comprising a phospholipid or a mixture of phospholipids selected from DOPC, POPC, SPC, EPC, PEG-DSPE or DOPG, and cholesterol, wherein cholesterol is present in an amount of 5-40 mole percent relative to the delivery vehicle; and
   (b) one or more therapeutic agent,
   wherein 50-90% of the therapeutic agent is in non-associated form and the weight ratio of the phospholipid and cholesterol in combination to the therapeutic agent is 5-80 to 1.

2. The method of claim 1, wherein the therapeutic agent is an antagonist specific to VEGF.

3. The method of claim 2, wherein the antagonist specific to VEGF is an antibody specific to VEGF, a VEGF receptor, a nucleic acid or a small molecule.

4. The method of claim 3, wherein the antibody specific to VEGF is a naturally occurring immunoglobulin, a functional fragment thereof, a humanized antibody, a chimeric antibody, a diabody or a single chain antibody.

5. The method of claim 3, wherein, the antibody specific to VEGF is Avastin.

6. The method of claim 3, wherein the antibody specific to VEGF is a Fab, Fab', F(ab)$_2$ or F(ab')2 fragment.

7. The method of claim 1, wherein the therapeutic agent is an anti-inflammation molecule.

8. The method of claim 7, wherein the anti-inflammation molecule is a corticosteroid.

9. The method of claim 1, wherein the delivery vehicle and the therapeutic agent are admixed and in lyophilized form.

10. The method of claim 1, wherein the delivery vehicle and the therapeutic agent for the eye are separate.

11. The method of claim 10, wherein the delivery vehicle is in lyophilized form.

12. The method of claim 11, which includes:
    suspending the delivery vehicle and the therapeutic agent in an aqueous solution to form the composition in a form of aqueous suspension.

13. The method of claim 1, wherein 60-90% of the therapeutic agent is in non-associated form and the weight ratio of the phospholipid and cholesterol in combination to the therapeutic agent is 5-40 to 1.

14. The method of claim 1, wherein the mixture of phospholipids is a mixture of a first phospholipid and a second phospholipid, the first phospholipid being DOPC, POPC, SPC, or EPC and the second phospholipid being PEG-DSPE or DOPG.

15. The method of claim 14, wherein the first phospholipid is DOPC and the second phospholipid is DOPG.

16. The method of claim 15, wherein the mole percent of DOPC is 29.5% to 90% and the mole percent of DOPG is 3% to 37.5% relative to the delivery vehicle.

17. The method of claim 14, wherein the first phospholipid is POPC and the second phospholipid is PEG-DSPE or DOPG.

18. The method of claim 1, wherein the mole percent of cholesterol is 10-33% relative to the delivery vehicle.

19. The method of claim 1, wherein the mole percent of cholesterol is 20-25% relative to the delivery vehicle.

* * * * *